United States Patent
Hara et al.

(10) Patent No.: US 9,315,435 B2
(45) Date of Patent: Apr. 19, 2016

(54) METHOD FOR PRODUCING HYDROXYPHENYLCYCLOHEXANOL COMPOUND

(71) Applicant: Sumitomo Chemical Company, Limited, Tokyo (JP)

(72) Inventors: Takeshi Hara, Osaka (JP); Yoshihiko Iwanaga, Osaka (JP)

(73) Assignee: Sumitomo Chemical Company, Limited, Tokyo (JP)

(*) Notice: Subject to any disclaimer, the term of this patent is extended or adjusted under 35 U.S.C. 154(b) by 0 days.

(21) Appl. No.: 14/395,971

(22) PCT Filed: Apr. 8, 2013

(86) PCT No.: PCT/JP2013/061133
§ 371 (c)(1),
(2) Date: Oct. 21, 2014

(87) PCT Pub. No.: WO2013/161594
PCT Pub. Date: Oct. 31, 2013

(65) Prior Publication Data
US 2015/0141707 A1  May 21, 2015

(30) Foreign Application Priority Data
Apr. 24, 2012 (JP) ................................ 2012-098456

(51) Int. Cl.
*C07C 37/00* (2006.01)
(52) U.S. Cl.
CPC ............. *C07C 37/00* (2013.01); *C07C 2101/14* (2013.01)
(58) Field of Classification Search
CPC .................................................... C07C 37/00
See application file for complete search history.

(56) References Cited

U.S. PATENT DOCUMENTS

| 6,313,351 B1 | 11/2001 | Kiya et al. | |
| 2015/0099901 A1* | 4/2015 | Ohno | C07C 29/20 568/816 |

FOREIGN PATENT DOCUMENTS

| JP | H01-160930 A | 6/1989 | |
| JP | 2001-089405 A | 4/2001 | |
| JP | 2001-192349 A | 7/2001 | |
| JP | 2006-036752 A | 2/2006 | |
| WO | WO 2013/153957 A1 * | 10/2013 | ............ C07C 29/78 |

OTHER PUBLICATIONS

Database CAPLUS in STN, Acc. No. 1970:498456, Khorgami, Quarterly Bulletin of the Faculty of Science, Tehran University (1970), 3, pp. 1-6 (abstract).*
Tsukinoki et al., Tetrahedron Letters (2000), 41, pp. 5865-5868.*
Jones et al., Journal of the Chemical Society (1950), pp. 1836-1841.*
Wilds et al., Journal of the American Chemical Society (1954), 76, pp. 1733-1736.*
International Search Report issued Jun. 18, 2013 in International Application No. PCT/JP2013/061133.
Zheng et al. Catalytic transfer hydrogenation and its application in organic synthesis. Industrial Catalysis, 12(3), p. 29-35 (2004).

* cited by examiner

*Primary Examiner* — Brian J Davis
(74) *Attorney, Agent, or Firm* — Panitch Schwarze Belisario & Nadel LLP

(57) ABSTRACT

A method comprising a step of stirring a composition containing a biphenol compound represented by the formula (1):

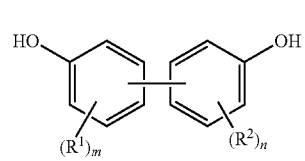

wherein, $R^1$ and $R^2$ represent each independently an alkyl group having 1 to 3 carbon atoms, and m and n represent each independently an integer of 0 to 2, a secondary alcohol and a nickel catalyst, for producing a hydroxyphenylcyclohexanol compound represented by the formula (2):

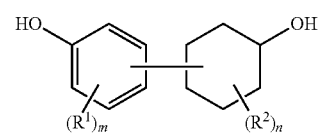

wherein, $R^1$, $R^2$, m and n represent the same meaning as described above, with the proviso that the above-described secondary alcohol has a different structure from that of the hydroxyphenylcyclohexanol compound represented by the above-described formula (2).

7 Claims, No Drawings

METHOD FOR PRODUCING HYDROXYPHENYLCYCLOHEXANOL COMPOUND

CROSS-REFERENCE TO RELATED APPLICATION

This application is a Section 371 of International Application No. PCT/JP2013/061133, filed Apr. 8, 2013, which was published in the Japanese language on Oct. 31, 2013, under International Publication No. WO 2013/161594 A1, and the disclosure of which is incorporated herein by reference.

TECHNICAL FIELD

The present invention relates to a method for producing a hydroxyphenylcyclohexanol compound.

BACKGROUND ART

A hydroxyphenylcyclohexanol compound is useful as a raw material of various medicines and industrial chemicals. Patent document 1 describes a method for producing 4-(4-hydroxyphenyl)cyclohexanol by catalytically hydrogenating 4,4'-biphenol using as a catalyst palladium carbon having undergone a treatment for changing activity. Non-patent document 1 describes a method for producing 4-(4-hydroxyphenyl)cyclohexanol from 4,4'-biphenol under atmospheric pressure at a temperature of 90° C. using a nickel-aluminum alloy in the presence of a 1 mass % potassium hydroxide aqueous solution.

PRIOR ART DOCUMENT

Patent Document

[Patent document 1] JP-A No. 2001-192349

Non-Patent Document

[Non-patent document 1] Tetrahedron Letters, 41 (2000) 5865

SUMMARY OF THE INVENTION

Problem to be Solved by the Invention

However, the production methods described in patent document 1 and non-patent document 1 are not always satisfactory methods as an industrial production method, and a novel method for producing a hydroxyphenylcyclohexanol compound has been required.

Means for Solving the Problem

The present invention includes the following inventions.
[1] A method comprising a step of stirring a composition containing
a biphenol compound represented by the formula (1):

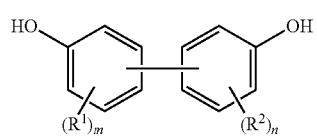

wherein, $R^1$ and $R^2$ represent each independently an alkyl group having 1 to 3 carbon atoms, and m and n represent each independently an integer of 0 to 2,
a secondary alcohol and
a nickel catalyst,
for producing a hydroxyphenylcyclohexanol compound represented by the formula (2):

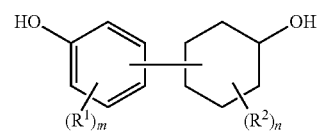

wherein, $R^1$, $R^2$, m and n represent the same meaning as described above,
with the proviso that the above-described secondary alcohol has a different structure from that of the hydroxyphenylcyclohexanol compound represented by the above-described formula (2).

[2] The method according to [1], wherein the amount of the secondary alcohol is from 2 parts by mass to 5 parts by mass with respect to 1 part by mass of the biphenol compound.

[3] The method according to [1] or [2], wherein the nickel catalyst is a heterogeneous nickel catalyst.

[4] The method according to any one of [1] to [3], wherein the nickel catalyst is Raney nickel.

[5] The method according to any one of [1] to [4], wherein the amount of the nickel catalyst is from 0.1 part by mass to 0.5 parts by mass with respect to 1 part by mass of the biphenol compound.

[6] The method according to any one of [1] to [5], wherein the above-described biphenol compound is a biphenol compound represented by the formula (3):

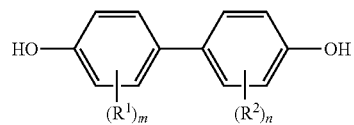

wherein, $R^1$, $R^2$, m and n represent the same meaning as described above.

[7] The method according to anyone of [1] to [6], wherein the biphenol compound is 4,4'-biphenol.

[8] A method comprising a step of stirring a composition containing
a biphenol compound represented by the formula (1):

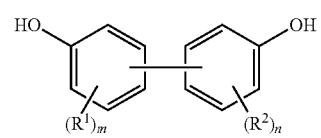

wherein, $R^1$ and $R^2$ represent each independently an alkyl group having 1 to 3 carbon atoms, and m and n represent each independently an integer of 0 to 2, and
a nickel catalyst
under pressurization with hydrogen while thermally insulating at 100° C. to 300° C., for producing a hydroxyphenylcyclohexanol compound represented by the formula (2):

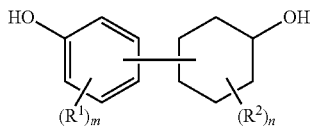
(2)

wherein, $R^1$, $R^2$, m and n represent the same meaning as described above.

[9] The method according to [8], wherein the composition contains no base.

[10] The method according to [8] or [9], wherein the hydrogen pressure under pressurization with hydrogen is from 2 kg/cm$^2$ to 200 kg/cm$^2$.

[11] The method according to any one of [8] to [10], wherein the nickel catalyst is a heterogeneous nickel catalyst.

[12] The method according to any one of [8] to [11], wherein the nickel catalyst is Raney nickel.

[13] The method according to any one of [8] to [12], wherein the amount of the nickel catalyst is from 0.1 part by mass to 0.5 parts by mass with respect to 1 part by mass of the biphenol compound.

[14] The method according to any one of [8] to [13], wherein the above-described biphenol compound is a biphenol compound represented by the formula (3):

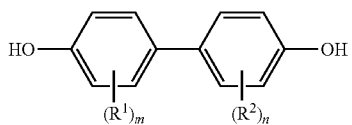
(3)

wherein, $R^1$, $R^2$, m and n represent the same meaning as described above.

[15] The method according to any one of [8] to [14], wherein the biphenol compound is 4,4'-biphenol.

[16] The method according to any one of [8] to [15], wherein the composition further contains an organic solvent.

[17] The method according to [16], wherein the organic solvent is an aliphatic monohydric alcohol.

Effect of the Invention

The present invention provides a novel method for producing a hydroxyphenylcyclohexanol compound.

MODES FOR CARRYING OUT THE INVENTION

The present invention is illustrated in detail below.

The present invention comprises a step of stirring a composition containing a biphenol compound represented by the formula (1) (hereinafter, sometimes referred to as compound (1)), a secondary alcohol and a nickel catalyst (hereinafter, sometimes referred to as composition (1)).

$R^1$ and $R^2$ represent each independently an alkyl group having 1 to 3 carbon atoms. The alkyl group having 1 to 3 carbon atoms includes a methyl group, an ethyl group, a propyl group and an isopropyl group. A methyl group is preferable.

It is preferable that $R^1$ and $R^2$ both represent a methyl group.

m and n represent each independently an integer of 0 to 2, preferably 0 or 1, more preferably 0.

The compound (1) is preferably a biphenol compound represented by the formula (3):

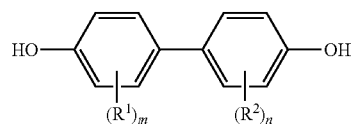
(3)

wherein, $R^1$, $R^2$, m and n represent the same meaning as described above, (hereinafter, sometimes referred to as compound (3)).

Examples of the compound (1) include specifically 4,4'-biphenol, 2,2'-dimethyl-4,4'-biphenol, 2,2',6,6'-tetramethyl-4,4'-biphenol, 2,2'-diethyl-4,4'-biphenol, 2,2',6,6'-tetraethyl-4,4'-biphenol, 2,2'-dipropyl-4,4'-biphenol, 2,2',6,6'-tetrapropyl-4,4'-biphenol, 2,2'-diisopropyl-4,4'-biphenol, 2,2',6,6'-tetraisopropyl-4,4'-biphenol;

3,3'-biphenol, 2,2'-dimethyl-3,3'-biphenol, 4,4'-dimethyl-3,3'-biphenol, 5,5'-dimethyl-3,3'-biphenol, 6,6'-dimethyl-3,3'-biphenol, 2,2'-diethyl-3,3'-biphenol, 4,4'-diethyl-3,3'-biphenol, 5,5'-diethyl-3,3'-biphenol, 6,6'-diethyl-3,3'-biphenol, 2,2'-dipropyl-3,3'-biphenol, 4,4'-dipropyl-3,3'-biphenol, 5,5'-dipropyl-3,3'-biphenol, 6,6'-dipropyl-3,3'-biphenol, 2,2'-diisopropyl-3,3'-biphenol, 4,4'-diisopropyl-3,3'-biphenol, 5,5'-diisopropyl-3,3'-biphenol, 6,6'-diisopropyl-3,3'-biphenol, 2,2',4,4'-tetramethyl-3,3'-biphenol, 2,2',5,5'-tetramethyl-3,3'-biphenol, 2,2',6,6'-tetramethyl-3,3'-biphenol, 2,2',4,4'-tetraethyl-3,3'-biphenol, 2,2',5,5'-tetraethyl-3,3'-biphenol, 2,2',6,6'-tetraethyl-3,3'-biphenol, 2,2',4,4'-tetrapropyl-3,3'-biphenol, 2,2',5,5'-tetrapropyl-3,3'-biphenol, 2,2',6,6'-tetrapropyl-3,3'-biphenol, 2,2',4,4'-tetraisopropyl-3,3'-biphenol, 2,2',5,5'-tetraisopropyl-3,3'-biphenol, 2,2',6,6'-tetraisopropyl-3,3'-biphenol;

2,2'-biphenol, 3,3'-dimethyl-2,2'-biphenol, 4,4'-dimethyl-2,2'-biphenol, 5,5'-dimethyl-2,2'-biphenol, 6,6'-dimethyl-2,2'-biphenol, 3,3'-diethyl-2,2'-biphenol, 4,4'-diethyl-2,2'-biphenol, 5,5'-diethyl-2,2'-biphenol, 6,6'-diethyl-2,2'-biphenol, 3,3'-dipropyl-2,2'-biphenol, 4,4'-dipropyl-2,2'-biphenol, 5,5'-dipropyl-2,2'-biphenol, 6,6'-dipropyl-2,2'-biphenol, 3,3'-diisopropyl-2,2'-biphenol, 4,4'-diisopropyl-2,2'-biphenol, 5,5'-diisopropyl-2,2'-biphenol, 6,6'-diisopropyl-2,2'-biphenol, 3,3',4,4'-tetramethyl-2,2'-biphenol, 2,2',5,5'-tetramethyl-2,2'-biphenol, 3,3',6,6'-tetramethyl-2,2'-biphenol, 3,3',4,4'-tetraethyl-2,2'-biphenol, 3,3',5,5'-tetraethyl-2,2'-biphenol, 3,3',6,6'-tetraethyl-2,2'-biphenol, 3,3',4,4'-tetrapropyl-2,2'-biphenol, 3,3',5,5'-tetrapropyl-2,2'-biphenol, 3,3',6,6'-tetrapropyl-2,2'-biphenol, 3,3',4,4'-tetraisopropyl-2,2'-biphenol, 3,3',5,5'-tetraisopropyl-2,2'-biphenol and 3,3',6,6'-tetraisopropyl-2,2'-biphenol.

Preferably, 2,2'-biphenol, 3,3'-biphenol, 4,4'-biphenol, 2,2'-dimethyl-4,4'-biphenol and 2,2',6,6'-tetramethyl-4,4'-biphenol are listed.

More preferably, 4,4'-biphenol is mentioned.

These compounds (1) are available as marketed products or by production according to any known methods.

Examples of the nickel catalyst include Raney nickel, Urushibara nickel, nickel/diatomaceous earth, nickel/alumina, nickel/silica and bis(triphenylphosphine)nickel dichloride. Preferably, "heterogeneous nickel catalysts" such as Raney nickel, Urushibara nickel, nickel/diatomaceous earth, nickel/alumina, and nickel/silica are listed. More preferably, Raney nickel is mentioned.

As the above-described nickel catalyst, those commercially marketed as general-purpose catalysts for hydrogenation can be used. Specifically, Raney (registered trademark) catalyst available from W. R. Grace and Company and Nickel sponge catalyst are listed. Further, one obtained by adding a trace amount of a metal component other than nickel, such as Cu, Cr, Mo, Mg and Al, as a co-catalyst to a nickel catalyst may also be used.

The nickel catalysts may be used singly or in combination.

The amount of the nickel catalyst is usually in the range of 0.001 part by mass to 20 parts by mass, preferably 0.01 part by mass to 2.0 parts by mass, more preferably 0.1 part by mass to 0.5 part by mass, further preferably 0.1 part by mass to 0.3 part by mass, with respect to 1 part by mass of the compound (1).

The secondary alcohol in the present invention acts as a hydrogen source, and has a structure different from that of a hydroxyphenylcyclohexanol compound represented by the formula (2) (hereinafter, sometimes referred to as compound (2)) and also different from that of bicyclohexanediol which can be generated as a by-product. The secondary alcohol is preferably an aliphatic monohydric alcohol, and specific examples thereof include 2-propanol, 2-butanol, 2-pentanol, 3-pentanol, 2-hexanol, 3-hexanol, cyclohexanol, 2-heptanol, 3-heptanol, 2-octanol, 4-decanol, 2-dodecanol, 3-methyl-2-butanol, 3,3-dimethyl-2-butanol, 3-methyl-2-pentanol, 5-methyl-2-hexanol and 4-methyl-3-heptanol. More preferably, 2-propanol and 2-butanol are listed, and further preferably, 2-propanol is mentioned.

The secondary alcohols may be used singly or in combination.

The amount of the secondary alcohol is usually from 1 part by mass to 100 parts by mass, preferably from 1 part by mass to 50 parts by mass, more preferably from 2 parts by mass to 5 parts by mass, further preferably from 2 parts by mass to 3 parts by mass, with respect to 1 part by mass of the compound (1).

The composition (1) may contain an organic solvent other than the secondary alcohol. Examples of the organic solvent include saturated hydrocarbon solvents such as pentane, hexane, cyclohexane, heptane, octane, nonane, and decane; aromatic hydrocarbon solvents such as toluene, ethylbenzene, xylene, and mesitylene; alcohol solvents such as methanol, ethanol, propanol, butanol, pentanol, hexanol, ethylene glycol, propylene glycol, 2-methyl-2-propanol, 2-methyl-2-butanol, 2,3-dimethyl-2-butanol, 2-methyl-2-pentanol, 3-methyl-3-pentanol, 3-ethyl-3-pentanol, 2,3-dimethyl-3-pentanol, 3-ethyl-2,2-dimethyl-3-pentanol, 2-methyl-2-hexanol, and 3,7-dimethyl-3-octanol; aprotic polar solvents such as N,N-dimethylformamide, N,N-dimethylacetamide, N-methylpyrrolidone, acetonitrile, benzonitrile, and dimethyl sulfoxide; and, ether solvents such as diethyl ether, tert-butyl methyl ether, 1,2-dimethoxyethane, 1,4-dioxane, tetrahydrofuran, and anisole.

The above-described organic solvents may be used singly or in combination.

The amount of the organic solvent is usually from 0.01 part by mass to 100 parts by mass, preferably from 0.1 part by mass to 50 parts by mass, more preferably from 0.1 part by mass to 5 parts by mass, with respect to 1 part by mass of the compound (1).

Stirring is conducted usually with heating. The temperature in stirring is usually in the range of 100° C. to 300° C., preferably in the range of 100° C. to 200° C., more preferably in the range of 110° C. to 140° C.

When the composition (1) is stirred, the compound (1) reacts to generate the compound (2). Progress of the reaction can be confirmed by measuring the decrease amount of the compound (1) or the generation amount of the compound (2) by analysis means such as gas chromatography and liquid chromatography. It is preferable that stirring is stopped to terminate the reaction when the amount of an unreacted compound (1) with respect to the amount of the compound (1) used in the reaction reaches 5 mass % to 15 mass %. Specifically, there is mentioned, for example, a method in which stirring is stopped to terminate the reaction when the percentage of the area of gas chromatography of an unreacted compound (1) with respect to the area of gas chromatography of the compound (1) in the composition (1) before the reaction reaches 5% to 15%.

The reaction is carried out usually under an inert gas atmosphere, and preferably carried out in the absence of a hydrogen gas. Examples of the inert gas include nitrogen and argon, and nitrogen is preferable.

The reaction time is usually from 1 hour to 150 hours.

The reaction vessel is not particularly restricted, and it is preferable to use a pressure-proof vessel such as an autoclave if it is used under reaction conditions of remarkable pressurization in the reaction vessel such as a case in which the temperature in stirring is higher than the boiling point of the above-described secondary alcohol or organic solvent.

After completion of the reaction, for example, an organic solvent is added to the reaction mixture to dissolve the compound (2), then, insoluble components are removed by filtration, and the organic solvent is distilled off from the resultant filtrate, thus the compound (2) can be obtained.

The compound (2) may be further purified by usual purification means such as re-crystallization.

Further, the present invention comprises a step of stirring a composition containing the compound (1) and a nickel catalyst (hereinafter, sometimes referred to as composition (2)) under pressurization with hydrogen while thermally insulating at 100° C. to 300° C.

Examples of $R^1$, $R^2$, m, n, the compound (1), the compound (3) and the nickel catalyst each include the same as those contained in the above-described composition (1).

It is preferable that the composition (2) contains no base.

It is preferable that the composition (2) contains an organic solvent. Examples of the organic solvent include alcohol solvents such as methanol, ethanol, n-propanol, 2-propanol, n-butanol, 2-butanol, ethylene glycol, propylene glycol, 2-pentanol, 3-pentanol, 2-hexanol, 3-hexanol, cyclohexanol, 2-heptanol, 3-heptanol, 2-octanol, 4-decanol, 2-dodecanol, 3-methyl-2-butanol, 3,3-dimethyl-2-butanol, 3-methyl-2-pentanol, 5-methyl-2-hexanol, 4-methyl-3-heptanol, 2-methyl-2-propanol, 2-methyl-2-butanol, 2,3-dimethyl-2-butanol, 2-methyl-2-pentanol, 3-methyl-3-pentanol, 3-ethyl-3-pentanol, 2,3-dimethyl-3-pentanol, 3-ethyl-2,2-dimethyl-3-pentanol, 2-methyl-2-hexanol, and 3,7-dimethyl-3-octanol; aprotic polar solvents such as N,N-dimethylformamide, N,N-dimethylacetamide, N-methylpyrrolidone, acetonitrile, benzonitrile, and dimethyl sulfoxide; ether solvents such as diethyl ether, tert-butylmethyl ether, 1,2-dimethoxyethane, 1,4-dioxane, tetrahydrofuran, and anisole; and, halogenated hydrocarbon solvents such as chloroform, dichloromethane, and 1,2-dibromoethane. Preferably, aliphatic monohydric alcohols are listed, and more preferably, 2-propanol and 2-butanol are mentioned.

The above-described organic solvents may be used singly or in combination.

The amount of the organic solvent is usually from 0.01 part by mass to 100 parts by mass, preferably from 0.1 part by mass to 50 parts by mass, more preferably from 0.1 part by mass to 5 parts by mass, with respect to 1 part by mass of the compound (1)

Stirring is conducted usually with heating. The temperature in stirring is usually in the range of 100° C. to 300° C., preferably in the range of 100° C. to 200° C., more preferably in the range of 120° C. to 180° C.

The pressure in pressurization with hydrogen is usually in the range of 2 kg/cm$^2$ to 200 kg/cm$^2$, preferably in the range of 3 kg/cm$^2$ to 50 kg/cm$^2$, more preferably in the range of 3 kg/cm$^2$ to 10 kg/cm$^2$. Examples of the reaction vessel include pressure-proof vessels such as an autoclave.

When the composition (2) is stirred under pressurization with hydrogen while thermally insulating at 100° C. to 300° C., the compound (1) reacts to generate the compound (2). Progress of the reaction can be confirmed by the same method as for the above-described composition (1), and it is preferable to terminate the reaction at the time when the similar reaction has progressed. Further, progress of the reaction can be confirmed also based on the amount of hydrogen consumption. It is preferable to terminate the reaction when 0.9-fold mol to 1.4-fold mol of hydrogen of the theoretical hydrogen absorption amount (3-fold mol of the compound (1)) has been consumed. The reaction time is usually 1 hour to 150 hours.

Examples of the reaction vessel include pressure-proof vessels such as an autoclave.

After completion of the reaction, for example, an organic solvent is added to the reaction mixture to dissolve the compound (2), then, insoluble components are removed by filtration, and the organic solvent is distilled off from the resultant filtrate, thus the compound (2) can be obtained.

The compound (2) may be further purified by usual purification means such as re-crystallization.

EXAMPLES

The present invention is illustrated further in detail by examples below.

Example 1

Production example of hydroxyphenylcyclohexanol represented by the formula (2-1):

(2-1)

(hereinafter, sometimes referred to as compound (2-1))

Into a vessel of a stainless autoclave having a content volume of 750 mL were added 50.00 g (268.51 mmol) of 4,4'-biphenol, 15.00 g of a Raney nickel catalyst (R-2311 manufactured by Nikko Rika Corporation, weighed as water slurry) and 150.00 g of 2-propanol at a room temperature of about 25° C. An atmosphere in the vessel containing the resultant mixture was purged sufficiently with a nitrogen gas, then, the mixture was heated up to 120° C. and stirred while thermally insulating for 12 hours. Thereafter, the resultant mixture was cooled down to room temperature, 100.00 g of tetrahydrofuran was added, and the mixture was stirred, then, solid components were removed by filtration. The resultant filtrate was analyzed by gas chromatography and the production rate of the compound (2-1) as the intended product was calculated, to find 79% by mol with respect to the raw material 4,4'-biphenol, and the production rate of bicyclohexanediol as a by-product which is difficult to be separated and removed was calculated, to find 4.8% by mol with respect to the raw material 4,4'-biphenol.

Example 2

Into a vessel of a stainless autoclave having a content volume of 100 mL were added 5.00 g (26.85 mmol) of 4,4'-biphenol, 0.65 g of a Raney nickel catalyst (manufactured by Tokyo Chemical Industry Co., Ltd., weighed as water slurry) and 15.00 g of 2-propanol at a room temperature of about 25° C. An atmosphere in the vessel containing the resultant mixture was purged sufficiently with a hydrogen gas, then, the mixture was heated up to 140° C. and the hydrogen gas pressure was adjusted to 7 kg/cm$^2$. The mixture was stirred while thermally insulated for 8 hours while controlling so that the hydrogen gas pressure in the system was kept at 7 kg/cm$^2$ by additionally adding a hydrogen gas as needed. Thereafter, the resultant mixture was cooled down to room temperature, and the atmosphere was purged with a nitrogen gas. Then, into the system purged with a nitrogen gas was added 25.00 g of tetrahydrofuran, the resultant mixture was stirred, then, solid components were removed by filtration. The resultant filtrate was analyzed by a liquid chromatography internal standard method (internal standard: n-propyl benzoate), and the content of the compound (2-1) in the filtrate was calculated. As a result, the yield of the compound (2-1) based on 4,4'-biphenol was 98.4% by mol. Further, the resultant filtrate was analyzed by gas chromatography and the production rate of the compound (2-1) as the intended product was calculated, to find 86% by mol with respect to the raw material 4,4-biphenol, and the production rate of bicyclohexanediol as a by-product which is difficult to be separated and removed was calculated, to find 7.7% by mol with respect to the raw material 4,4'-biphenol.

Example 3

Into a vessel of a stainless autoclave having a content volume of 100 mL were added 5.00 g (26.85 mmol) of 4,4'-biphenol, 1.52 g of a Raney nickel catalyst (manufactured by Tokyo Chemical Industry Co., Ltd., weighed as water slurry) and 15.00 g of 2-propanol at a room temperature of about 25° C. An atmosphere in the vessel containing the resultant mixture was purged sufficiently with a hydrogen gas, then, the mixture was heated up to 120° C. and the hydrogen gas pressure was adjusted to 5 kg/cm$^2$. The mixture was stirred while thermally insulated for 8 hours while controlling so that the hydrogen gas pressure in the system was kept at 5 kg/cm$^2$ by additionally adding a hydrogen gas as needed. After completion of the reaction, the resultant mixture was cooled down to room temperature, and the atmosphere was purged with a nitrogen gas. Then, into the system purged with a nitrogen gas was added 25.00 g of tetrahydrofuran, the resultant mixture was stirred, then, solid components were removed by filtration. The resultant filtrate was analyzed in the same manner as in Example 2. As a result, the yield of the compound (2-1) based on 4,4'-biphenol was 98.2% by mol. Further, the resultant filtrate was analyzed by gas chromatography and the production rate of the compound (2-1) as the intended product was calculated, to find 82% by mol with respect to the raw material 4,4'-biphenol, and the production rate of bicyclohexanediol as a by-product which is difficult to be separated and removed was calculated, to find 4.1% by mol with respect to the raw material 4,4'-biphenol.

INDUSTRIAL APPLICABILITY

The present invention is useful as a novel method of producing a hydroxyphenylcyclohexanol compound.

The invention claimed is:

1. A method comprising a step of stirring a composition containing a biphenol compound represented by the formula (1):

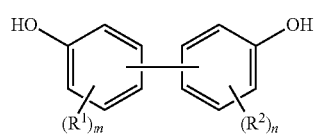

wherein, $R^1$ and $R^2$ represent each independently an alkyl group having 1 to 3 carbon atoms, and m and n represent each independently an integer of 0 to 2,
a secondary alcohol and
a nickel catalyst,
in the absence of a hydrogen gas, for producing a hydroxyphenylcyclohexanol compound represented by the formula (2):

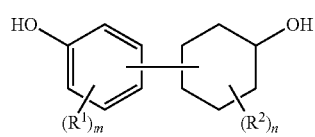

wherein, $R^1$, $R^2$, m and n represent the same meaning as described above, with the proviso that said secondary alcohol has a different structure from that of the hydroxyphenylcyclohexanol compound represented by said formula (2).

2. The method according to claim 1, wherein the amount of the secondary alcohol is from 2 parts by mass to 5 parts by mass with respect to 1 part by mass of the biphenol compound.

3. The method according to claim 1, wherein the nickel catalyst is a heterogeneous nickel catalyst.

4. The method according to claim 1, wherein the nickel catalyst is Raney nickel.

5. The method according to claim 1, wherein the amount of the nickel catalyst is from 0.1 part by mass to 0.5 parts by mass with respect to 1 part by mass of the biphenol compound.

6. The method according to claim 1, wherein said biphenol compound is a biphenol compound represented by the formula (3):

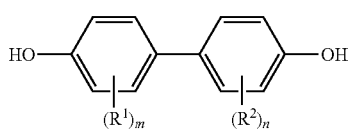

wherein, $R^1$, $R^2$, m and n represent the same meaning as described above.

7. The method according to claim 1, wherein the biphenol compound is 4,4'-biphenol.

* * * * *